United States Patent
Kawato et al.

(10) Patent No.: US 6,919,478 B2
(45) Date of Patent: Jul. 19, 2005

(54) REACTION TUBE, PROCESS FOR PRODUCING CATALYST AND PROCESS FOR PRODUCING UNSATURATED ALDEHYDE AND UNSATURATED CARBOXYLIC ACID

(75) Inventors: Seiichi Kawato, Hiroshima (JP); Masahide Kondo, Hiroshima (JP); Toru Kuroda, Hiroshima (JP); Masanori Nitta, Hiroshima (JP); Mieji Sugiyama, Hiroshima (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 1 day.

(21) Appl. No.: 10/467,343

(22) PCT Filed: Feb. 19, 2002

(86) PCT No.: PCT/JP02/01395

§ 371 (c)(1),
(2), (4) Date: Feb. 9, 2004

(87) PCT Pub. No.: WO02/066160

PCT Pub. Date: Aug. 29, 2002

(65) Prior Publication Data

US 2004/0116280 A1 Jun. 17, 2004

(30) Foreign Application Priority Data

Feb. 20, 2001 (JP) ........................................ 2001-043576

(51) Int. Cl.⁷ ...................... C07C 51/16; C07C 51/235; C07C 51/245; B01J 23/00
(52) U.S. Cl. ...................... 562/523; 562/537; 562/538; 562/542; 562/546; 502/311; 502/316; 422/312
(58) Field of Search .................................. 562/523, 537, 562/538, 542, 546; 502/311, 316; 422/312

(56) References Cited

U.S. PATENT DOCUMENTS

| | | | | | |
|---|---|---|---|---|---|
| 3,656,914 | A | * | 4/1972 | Friedrichsen et al. | 422/312 |
| 3,990,858 | A | * | 11/1976 | O'Sullivan et al. | 422/197 |
| 4,356,114 | A | | 10/1982 | Kadowaki et al. | |
| 4,559,207 | A | * | 12/1985 | Hiller et al. | 422/197 |
| 5,425,924 | A | * | 6/1995 | Finley | 422/220 |
| 6,046,343 | A | * | 4/2000 | Mummey et al. | 549/259 |
| 6,333,011 | B1 | * | 12/2001 | Schliephake et al. | 422/197 |
| 6,417,376 | B1 | * | 7/2002 | Yeh et al. | 549/248 |
| 6,479,691 | B1 | * | 11/2002 | Sasaki et al. | 558/321 |

FOREIGN PATENT DOCUMENTS

| | | |
|---|---|---|
| EP | 987057 | 3/2000 |
| JP | 2-83042 | 3/1990 |
| JP | 4-4048 | 1/1992 |
| JP | 08-182933 | 7/1996 |
| JP | 2000-070719 | 3/2000 |

* cited by examiner

Primary Examiner—Cam N. Nguyen
(74) Attorney, Agent, or Firm—Oblon, Spivak, McClelland, Maier & Neustadt, P.C.

(57) ABSTRACT

In producing a catalyst used for synthesis of an unsaturated aldehyde and an unsaturated carboxylic acid by a gas-phase catalytic oxidation, there is used a step of packing an additive-containing catalyst precursor of the catalyst into a tubular reactor, passing a gas through the tubular reactor, and elevating, in this state, the temperature of the additive-containing catalyst precursor so that a temperature of the gas at an outlet of the catalyst precursor layer becomes higher than a temperature of the gas at an inlet of the catalyst precursor layer. The step makes possible easy and highly reproducible production of a high-performance catalyst which is small in the reduction in catalytic performance caused by, for example, the thermal decomposition of the additive contained in the catalyst precursor.

13 Claims, No Drawings

REACTION TUBE, PROCESS FOR PRODUCING CATALYST AND PROCESS FOR PRODUCING UNSATURATED ALDEHYDE AND UNSATURATED CARBOXYLIC ACID

TECHNICAL FIELD

The present invention relates to a catalyst used in gas-phase catalytic oxidation of propylene, isobutylene, tert-butyl alcohol (hereinafter may be abbreviated to TBA), methyl tert-butyl ether (hereinafter may be abbreviated to MTBE) or the like with molecular oxygen to synthesize a corresponding unsaturated aldehyde and a corresponding unsaturated carboxylic acid; and a process for production of an unsaturated aldehyde and an unsaturated carboxylic acid using the catalyst. More particularly, the present invention relates to a heat treatment method used in production of the catalyst.

BACKGROUND ART

A number of proposals have heretofore been made on catalysts used in gas-phase catalytic oxidation of propylene to produce acrolein and acrylic acid, or on catalysts used in gas-phase catalytic oxidation of isobutylene, TBA or MTBE to produce methacrolein and methacrylic acid. Many proposals have been made as well on processes for producing such catalysts.

In, for example, JP-A-98143/1983, JP-A-109946/1991, etc. are reported processes which comprise adding, at the time of preparation of a catalyst precursor, an organic compound such as aniline, methylamine, pentaerythritol or the like in order to obtain a catalyst of controlled pore size. Also in JP-A-315147/1988, JP-A-4048/1992, etc. are reported processes which comprise adding a starch. These proposals have an advantage-that by applying a heat treatment, the organic compound added is removed and, by varying the size of the organic compound used, the pore diameters of the catalyst obtained can be controlled freely.

In the catalysts produced according to the processes described in the above literature, however, it may appear, when the pore diameters of catalyst are made larger for improved catalyst performance, that the molded catalyst has a low strength and, at its packing stage, gives rise to powdering and disintegration owing to the mechanical impact applied during the packing. When the powdering and disintegration appear at a striking proportion, a decrease in substantial packing volume of catalyst and/or an increase in pressure loss takes place and, resultantly, it may not be possible to carry out an intended reaction under predetermined conditions.

In general, when a molded catalyst of low strength is packed into a tubular reactor, there is employed, in many cases, a packing method wherein a countermeasure for preventing the powdering and disintegration of such a solid catalyst has been taken.

In, for example, JP-A-31351/1993 is disclosed a method of, in packing a solid catalyst into the tubular reactors inside a fixed bed reactor, dropping the solid catalyst with a string-like substance being interposed. Also in JP-A-64902/1994 and JP-A-24232/1998 are disclosed a method of using a catalyst cartridge and a method of using a catalyst filling machine having an openable or closable catalyst outlet. Further in JP-A-42400/2000 is disclosed a method of using a cylindrical container which has an inner wall of such a hardness as to show no deformation when a particulate substance has been fed thereinto and which has, at the bottom, an opening having an opening and closing mechanism.

In reactors of multi-tubular type used industrially, however, there are several thousands or more of tubular reactors in some cases; therefore, it is very complicated to carry out the operations described in the above literature, for each of the individual tubular reactors, and the methods described therein are not realistic.

In order to avoid such inconveniences, there are methods of packing, into a tubular reactor, an additive-containing catalyst precursor having a sufficient strength during the packing, then passing a gas through the tubular reactor, and, in this state, applying a heat treatment to the additive-containing catalyst precursor to remove the additive in the catalyst precursor.

In, for example, JP-A-358542/1992 and JP-A-182933/1996 are disclosed a method of coating at least part of the surface of a catalyst precursor with an organic polymer compound, and a method of using an additive-containing catalyst precursor obtained by impregnating, into the pores of a catalyst precursor, an organic compound which is a solid at normal temperature and melts at 300° C. or below or which is soluble in organic solvents. Also in the Examples of JP-A-70719/2000 is described a method of packing, into a tubular reactor, a catalyst precursor containing carboxymethyl cellulose or methyl cellulose ether and calcining the catalyst precursor at 510° C. for 3 hours with air being passed.

The study by the present inventors, however, revealed that, with the conventional methods described in the above literature, etc., a reduction in catalyst performance takes place in some cases and a problem remains in reproducible production of catalyst.

Hence, it is desired to develop a method for packing an additive-containing catalyst precursor into a tubular reactor and then applying a heat treatment to the catalyst precursor, which method gives a small reduction in catalytic performance and is simple and highly reproducible when applied industrially.

DISCLOSURE OF THE INVENTION

In view of the above situation, an object of the present invention is to provide an easy and well reproducible process for producing the high-performance catalyst with small reduction of the catalytic performance caused by, for example, the thermal decomposition of the additive contained in the catalyst precursor, while applying a heat treatment to the catalyst precursor, after packing the additive-containing catalyst precursor into a tubular reactor. The molded catalyst contains molybdenum, bismuth, iron, etc., and is used for gas-phase catalytic oxidation of propylene, isobutylene, TBA or MTBE for synthesis of the corresponding aldehyde and carboxylic acid.

In order to achieve the above aim, the present invention provides a tubular reactor filled with a catalyst for producing an unsaturated aldehyde and an unsaturated carboxylic acid by a gas-phase catalytic oxidation;

in which the catalyst is made by a process comprising the steps of;

packing an additive-containing catalyst precursor of the catalyst into the tubular reactor; and elevating a temperature of the additive-containing catalyst precursor, as passing a gas through the tubular reactor, so that a temperature of the gas at an outlet of the catalyst precursor layer is higher than a temperature of the gas at an inlet of the catalyst precursor layer.

The present invention also provides a process for producing a catalyst for producing an unsaturated aldehyde and an unsaturated carboxylic acid by a gas-phase catalytic oxidation, which comprises the steps of;

packing an additive-containing catalyst precursor into the tubular reactor; and elevating a temperature of the additive-containing catalyst precursor, as passing a gas through the tubular reactor, so that a temperature of the gas at an outlet of the catalyst precursor layer is higher than a temperature of the gas at an inlet of the catalyst precursor layer.

The present invention further provides a process for producing the unsaturated aldehyde and the unsaturated carboxylic acid, wherein, using the tubular reactor of the present invention, propylene, isobutylene, tert-butyl alcohol or methyl tert-butyl ether is catalytically oxidized in a gas-phase with a molecular oxygen.

In the present invention, there is no particular restriction as to the method for producing an additive-containing catalyst precursor to be packed into a tubular reactor. There can be mentioned, for example, a method of forming a catalyst precursor in an additive-containing state, and a method of allowing a molded catalyst precursor to contain an additive by coating, impregnation or the like. The method of forming a catalyst precursor in an additive-containing state is preferred. Incidentally, "catalyst precursor" refers to a catalyst before heat treatment for additive removal.

The obtained additive-containing catalyst precursor (called also as molded catalyst) is packed into a tubular reactor and is heat-treated with a gas being passed. The present invention is suitable when the gas passed contains oxygen; in this case, the additive is decomposed by the heating in the presence of oxygen and the decomposed substances, vaporized substances, etc. generated mainly by the thermal decomposition of the additive are removed by the flow of the gas. Here, the heat treatment of the additive-containing catalyst precursor includes a temperature elevation step and, in at least a certain period of the step of elevating the temperature of the additive-containing catalyst precursor, the temperature of the gas passed through the tubular reactor, at the outlet of the catalyst precursor layer is made higher than the temperature of the gas at the inlet of the catalyst precursor layer. To achieve it, a heat treatment method such as heating of the tubular reactor from outside is used. As a result, it is possible to produce a catalyst small in reduction in catalytic performance, easily at a high reproducibility.

The reason is presumed to be as follows. In general, when an additive-containing catalyst precursor is packed into a tubular reactor and is heat-treated with a gas being passed through the tubular reactor, the decomposed substances, vaporized substances, etc. generated from the additive in the additive-containing catalyst precursor are removed gradually starting from the gas inlet side of the catalyst precursor layer, and the removed substances are carried by the flow of the gas to the gas outlet side of the catalyst precursor layer. At this time, when the temperature of the gas at the outlet of the catalyst precursor layer is not higher than the temperature of the gas at the inlet of the catalyst precursor layer, part of the decomposed substances, vaporized substances, etc. generated from the additive tend to accumulate at the outlet side of lower temperature. As a result, the decomposed substances, vaporized substances, etc. accumulated may remain after the heat treatment, and, when the gas passed contains oxygen, part of the accumulated substances may cause violent combustion, giving rise to sintering or reduction of catalyst.

In contrast, when the temperature of the gas at the outlet of the catalyst precursor layer is higher than the temperature of the gas at the inlet of the catalyst precursor layer, the accumulation of the decomposed substances, vaporized substances, etc. generated from the additive, at the outlet side is prevented; this reduces the remaining of the decomposed substances, vaporized substances, etc. accumulated, after the heat treatment, or the violent combustion of part of the accumulated substances and resultant catalyst sintering or reduction.

BEST MODE FOR CARRYING OUT THE INVENTION

Preferred embodiments of the present invention are described below.

The catalyst produced by the process of the present invention is preferably used in a gas-phase catalytic oxidation of at least one kind of compound selected from the group consisting of propylene, isobutylene, tert-butyl alcohol and methyl tert-butyl ether, with molecular oxygen.

As the source for the molecular oxygen, there are mentioned pure oxygen, air, air enriched with pure oxygen, etc. of these, air is economical.

The catalyst is preferably one containing at least molybdenum, bismuth and iron.

Specifically, a catalyst having a composition represented by the following general formula is preferred:

$Mo_aBi_bFe_cM_dX_eY_fZ_gSi_hO_i$

In the above formula, Mo, Bi, Fe, Si and O are molybdenum, bismuth, iron, silicon and oxygen, respectively; M is at least either of cobalt and nickel; X is at least one kind of element selected from the group consisting of chromium, lead, manganese, calcium, magnesium, niobium, silver, barium, tin, tantalum and zinc; Y is at least one kind of element selected from the group consisting of phosphorus, boron, sulfur, selenium, tellurium, cerium, tungsten, antimony and titanium; and Z is at least one kind of element selected from the group consisting of lithium, sodium, potassium, rubidium, cesium and thallium. a, b, c, d, e, f, g, h and i are the atomic ratios of the individual elements; and when a=12, b=0.01 to 3, c=0.01 to 5, d=1 to 12, e=0 to 8, f=0 to 5, g=0.001 to 2, h=0 to 20, and i is the number of oxygen atoms necessary for satisfying the valences of other components.

As the raw material for each of the above catalyst components, there can be used, in combination, the oxide, sulfate, nitrate, carbonate, hydroxide, ammonium salt, halide, etc. of each component. AS the raw material for molybdenum, for example, there can be used ammonium paramolybdenate, molybdenum trioxide, etc.

As to the method for producing an additive-containing catalyst precursor containing the above catalyst components, there is no particular restriction.

In one method, first, an aqueous slurry containing the catalyst components is prepared by a method such as precipitation, oxides mixing or the like. The aqueous slurry is dried. There is no particular restriction as to the drying method, and a method such as evaporation-to-dryness, spray drying or the like is used to obtain a dry powder.

The dry powder is fired to obtain a fired material. There is no particular restriction as to the calcining method, and known calcining conditions can be used. The calcining is conducted ordinarily in a temperature range of 200° C. to 600° C., and the calcining time is determined appropriately depending upon the catalyst to be produced.

Successively, the fired material is mixed with water and/or an alcohol and the resulting mixture is subjected to wet molding. There is no particular restriction as to the method and shape of wet molding, and molding into a desired shape such as sphere, ring, column, star or the like can be conducted by using an ordinary wet-molding machine such as extruder, tumbling granulator or the like. The amount of the water and/or alcohol mixed is preferably 15 to 60 parts by mass per 100 parts by mass of the fired material.

At that time, a predetermined additive is added. The additive is preferably one which is easily decomposed when heated and generates such decomposed substances, vaporized substances, etc. as are easily carried by a gas flow. The additive is preferably at least one kind of compound selected from the group consisting of natural polysaccharides, cellulose, polystyrene, polymethyl (meth)acrylate, ammonium nitrate and their derivatives. Natural polysaccharides and cellulose derivatives are particularly preferred as the additive.

In some cases, there is mixed as necessary a filler which generates substantially no decomposed substance, vaporized substance or the like when heated, such as inorganic compound (e.g. graphite or diatomaceous earth), inorganic fiber (e.g. glass fiber, ceramic fiber or carbon fiber) or the like.

The wet-molded material is dried to obtain an additive-containing catalyst precursor. There is no particular restriction as to the drying method, but a drying method using a microwave and hot air in combination is preferred.

The additive-containing catalyst precursor is packed into a tubular reactor and subjected to a heat treatment. Prior to the packing, the additive-containing catalyst precursor may be diluted with an inert carrier such as silica, alumina, silica-alumina, silicon carbide, ceramic balls, stainless steel or the like.

As described previously, in the heat treatment of the additive-containing catalyst precursor, the temperature of the gas passed through the tubular reactor, at the outlet of the catalyst precursor layer is controlled so as to become higher than the temperature of the gas at the inlet of the catalyst precursor layer, in at least a certain period of the step of elevating the temperature of the additive-containing catalyst precursor. AS the means for the control, external heating is employed generally. The highest temperature reached by the catalyst precursor layer in the heat treatment is ordinarily 100° C. to 600° C., preferably 200° C. to 500° C. When the highest temperature reached by the catalyst precursor in the heat treatment is 100° C. or more, remaining in the catalyst, of part of the decomposed substances, vaporized substances, etc. of the additive is prevented, whereby the adverse effect on the synthesis of unsaturated aldehyde and unsaturated carboxylic acid can be prevented. When the highest temperature reached by the catalyst precursor in the heat treatment is 600° C. or less, the sintering of the catalyst caused by such a high temperature can be prevented and the reduction in catalytic performance can be prevented.

In the step of elevating the temperature of the additive-containing catalyst precursor, the timing at which the temperature of the gas passed through the tubular reactor, at the outlet of the catalyst precursor layer is made higher than the temperature of the gas at the inlet of the catalyst precursor layer, differs depending upon the additive used and cannot be determined simply. However, it is preferred that the temperature of the gas passed through the tubular reactor, at the outlet of the catalyst precursor layer is made higher than the temperature of the gas at the inlet of the catalyst precursor layer when, in the step of elevating the temperature of the additive-containing catalyst precursor, at least part of the additive-containing catalyst precursor in the tubular reactor has reached a temperature range in which there is observed generation of the decomposed substances, vaporized substances, etc. mainly from the additive in the additive-containing catalyst precursor.

The reason therefor is that by making the temperature of the gas passed through the tubular reactor, at the outlet of the catalyst precursor layer, higher than the temperature of the gas at the inlet of the catalyst precursor layer in a temperature range in which there is observed generation of the decomposed substances, vaporized substances, etc. from the additive, the accumulation of the decomposed substances, vaporized substances, etc. from the additive is prevented effectively.

For the same reason, it is more preferred that the temperature of the gas passed through the tubular reactor, at the outlet of the catalyst precursor layer is made higher than the temperature of the gas at the inlet of the catalyst precursor layer when, in the step of elevating the temperature of the additive-containing catalyst precursor, at least part of the additive-containing catalyst precursor in the tubular reactor has reached a temperature at which the generation of the decomposed substances, vaporized substances, etc. mainly from the additive in the additive-containing catalyst precursor becomes most violent.

It is also preferred that, in the step of heating the additive-containing catalyst precursor, at least some part of the additive-containing catalyst precursor is heated to at least a temperature at which the mass of the additive-containing catalyst precursor decreases most sharply owing mainly to the change of the additive.

As to the gas passed through the tubular reactor, there is no particular restriction as long as it can swiftly remove the substances derived from the additive in the additive-containing catalyst precursor and does not deteriorate the catalyst. AS the gas, there can be used, for example, pure oxygen, air, nitrogen, carbon dioxide, helium, steam and mixtures thereof.

There is no particular restriction as to the method for making the temperature of the gas passed through the tubular reactor, at the outlet of the catalyst precursor layer, higher than the temperature of the gas at the inlet of the catalyst precursor layer. However, a method of passing a heat medium round the tubular reactor is preferred, and particularly preferred is a method in which a preheated heat medium is passed round the tubular reactor containing a layer of the catalyst precursor, to a direction opposite to the direction of gas flow inside the tubular reactor, because, with this method, the temperature distribution in the catalyst precursor layer can be continuously increased from the inlet of the catalyst precursor layer toward the outlet of the catalyst precursor layer. In this case, the heat medium conducts heat exchange with the tubular reactor, the additive-containing catalyst precursor in the tubular reactor, and the gas passed through the tubular reactor, and thereby is cooled gradually while being passed from the gas outlet of the catalyst precursor layer toward the gas inlet of the catalyst precursor layer. As a result, the temperature of the gas inlet of the catalyst precursor layer is kept lower than the temperature of the gas outlet of the catalyst precursor layer.

There is other method in which the circumference of the tubular reactor is divided into a plurality of zones and the individual zones are independently subjected to temperature control. In a specific example of such a method, the circumference of the tubular reactor is divided into two sections, a catalyst precursor layer inlet side and a catalyst precursor layer outlet side; and a heat medium of relatively low temperature is allowed to be at the zone of catalyst precursor layer inlet side and a heat medium of relatively high temperature is allowed to be at the zone of catalyst precursor layer outlet side.

When the temperature of the catalyst precursor layer is elevated by passing a preheated heat medium round the tubular reactor containing a layer of the catalyst precursor, to a direction opposite to the direction of gas flow inside the tubular reactor, the initial temperature of the heat medium is preferably 20° C. to 400° C. Meanwhile, the temperature of the additive-containing catalyst precursor at the gas inlet is gradually elevated as the passing of the heat medium proceeds, and is elevated to a desired temperature of preferably 100° C. to 600° C. It is particularly preferred that the maximum difference between the temperatures of the gas passed through the tubular reactor, at the inlet and outlet of the catalyst precursor layer is 10° C. to 400° C. in order to effectively remove the decomposed substances, vaporized substances, etc. of the additive in the additive-containing catalyst precursor without impairing the property of the catalyst.

There is no particular restriction as to the method for elevating the temperature of the additive-containing catalyst precursor. When an additive generating a heat at the time of its removal is used in the catalyst precursor, a small temperature elevation rate is preferably employed so as to enable the sufficiently removal of the generated heat from the catalyst precursor layer to avoid the possible generation of high-temperature area and subsequent reduction in catalytic performance. Too small a temperature elevation rate, however, needs too long a time in the temperature elevation step; therefore, the elevating of the temperature of the additive-containing catalyst precursor is practically conducted so that the temperature elevation rate does not become excessively large. In elevating the temperature of the additive-containing catalyst precursor, the maximum temperature elevation per hour, of the catalyst precursor is preferably 100° C. or less. Also preferably, in a certain timing of the step of heating the additive-containing catalyst precursor, the temperature of the catalyst precursor is kept, by controlling the temperature of the heat medium, for at least one hour in a temperature range not lower than 50° C. but not higher than a temperature at which the mass of the additive-containing catalyst precursor decreases most sharply owing to the change of the additive in the catalyst precursor.

Also preferably, in elevating the temperature of the additive-containing catalyst precursor, the temperature of the gas passed through the tubular reactor, at the inlet of the catalyst precursor layer is elevated to at least a temperature at which the mass of the additive-containing catalyst precursor decreases most sharply owing mainly to the change of the additive in the catalyst precursor. Thereby, the accumulation of the decomposed substances, vaporized substances, etc. of the additive, at the gas outlet of the catalyst precursor can be prevented very effectively.

Any medium is usable as the heat medium used for heating the tubular reactor, as long as it is a gas or a liquid at the use temperature. There can be used, for example, air, nitrogen, superheated steam, molten salts, organic heat media and heated oils.

By using a tubular reactor of the present invention packed with the thus-produced catalyst and subjecting propylene, isobutylene, TBA, MTBE or the like to gas-phase catalytic oxidation, a corresponding aldehyde and a corresponding carboxylic acid can be produced.

The amount of the molecular oxygen fed at that time into the tubular reactor is preferably 0.5 to 3 moles per mole of propylene, isobutylene, TBA or MTBE.

The raw material gas is used preferably by diluting with an inert gas such as nitrogen or the like, and may contain steam, carbon dioxide, etc.

The reaction pressure is normal pressure to several atmospheric pressures. The reaction temperature can be selected in a range between 200° C. and 450° C., with a range between 250° C. and 400° C. being particularly preferred.

The present invention is described in more detail below by way of Examples. However, the present invention is in no way restricted by these Examples. AS to the chemical reagents, commercial products of high purity were used unless otherwise specified; and "parts" refer to parts by mass.

Analytical Methods Used

Analyses of reaction products were conducted by gas chromatography. Thermogravimetric analyses of additive-containing catalyst precursors were conducted at a temperature elevation rate of 20° C./hr using a thermogravimetric analyzer TGA-50 produced by Shimadzu Corporation.

The degree of conversion of the raw material olefin, TBA or MTBE used (hereinafter referred to as the conversion degree of raw material), and the selectivities of the unsaturated aldehyde and unsaturated carboxylic acid formed were calculated from the following formulas:

conversion degree of raw material (%)=100×B/A selectivity of unsaturated aldehyde (%)=100×C/B selectivity of unsaturated carboxylic acid (%)=100×D/B In the above formulas, A is the moles of the raw material olefin, TBA or MTBE fed; B is the moles of the raw material olefin, TBA or MTBE reacted; C is the moles of the unsaturated aldehyde formed; and D is the moles of the unsaturated carboxylic acid formed.

EXAMPLE 1

To 1,000 parts of pure water were added 500 parts of ammonium paramolybdenate, 12.4 parts of ammonium para-tungstate, 1.4 parts of potassium nitrate, 27.5 parts of antimony trioxide and 49.5 parts of bismuth trioxide. The resulting mixture was stirred with heating, to obtain a liquid A. Separately, to 1,000 parts of pure water were added 114.4 parts of ferric nitrate, 370.8 parts of cobalt nitrate and 21.1 parts of zinc nitrate in this order, to obtain a liquid B. The liquid B was added to the liquid A to obtain an aqueous slurry. The aqueous slurry was dried using a spray drier to obtain a dry powder. The dry powder was fired at 300° C. for 1 hour to obtain a fired material. 500 parts of the fired material was mixed with 160 parts of pure water and 20 parts of methyl cellulose. The resulting mixture was subjected to extrusion molding to obtain a ring-molded wet-molded material having an outer diameter of 5 mm, an inner diameter of 2 mm and an average length of 5 mm. The wet-molded material was dried by a drying method using, in combination, a microwave and hot air, to obtain an additive (methyl cellulose)-containing catalyst precursor. The temperature at which the generation of decomposed substances and/or vaporized substances from the additive-containing catalyst precursor was most violent, was 230° C. as measured by thermogravimetry.

The additive-containing catalyst precursor was packed in a stainless steel-made tubular reactor of 27.5 mm in inner diameter and 4 m in length having a mechanism for passing a heat medium round the circumference, which was provided parallel to a vertical direction.

Successively, an air of 30° C. was passed through the tubular reactor. In this state, an air preheated at 150° C. (hereinafter may be abbreviated to heat medium air) was passed as a heat medium round the tubular reactor to a direction opposite to the direction of the air passed through the tubular reactor. Immediately after the start of the passing of the preheated air, the temperature of the air passed through the tubular reactor, at the inlet of the catalyst precursor layer was 30° C., the temperature of the air at the outlet was 33° C., and the difference between the temperatures at the inlet and the outlet was 3° C. Passing of the preheated air was continued; 1 hour later, the temperature of the air passed through the tubular reactor, at the inlet of the catalyst precursor layer was 32° C., the temperature of the air at the outlet was 82° C., and the temperature at the outlet was 50° C. higher than the temperature at the inlet. Thereafter, the temperatures of the air passed through the tubular reactor and the heat medium air were increased each at a rate of 20° C./hr and, in this state, the heat treatment was continued for 11 hours. After 12 hours from the start of the heat treatment, the temperature of the air passed through the tubular reactor was 250° C., the temperature of the heat medium air was 370° C., the temperature of the air passed through the tubular reactor, at the inlet of the catalyst precursor layer was 276° C., the temperature of the air at the outlet was 358° C., and the temperature of the air at the outlet was 82° C. higher than the temperature of the air at the inlet. In the period, the maximum difference between the temperatures at the inlet and the outlet was 105° C. Also in the period, the maximum temperature increase per hour, of the catalyst precursor was 50° C.

Then, the temperatures of the air passed through the tubular reactor and the heat medium air were kept each at 510° C. for 6 hours, and the heat treatment of the additive-containing catalyst precursor was completed. At the completion of the heat treatment, the temperatures of the air passed through the tubular reactor, at the inlet and outlet of the catalyst precursor layer were each 510° C.

The thus-obtained catalyst had a metal composition of $Mo_{12}W_{0.2}Bi_{0.9}Fe_{1.2}Sb_{0.8}Co_{5.4}Zn_{0.3}K_{0.06}$. The catalyst was cooled to 310° C., after which a raw material gas consisting of 5% of propylene, 12% of oxygen, 10% of steam and 73% of nitrogen (% was by volume) was passed through the catalyst layer for a contact time of 3.6 seconds, to give rise to a reaction. As a result, the degree of conversion of propylene was 98.9%; the selectivity of acrolein was 87.2%; and the selectivity of acrylic acid was 6.0%.

It became clear from the above that the sintering of catalyst caused by the combustion of additive, the reduction of catalyst by additive, etc. were prevented in the step of catalyst heat treatment and that a catalyst superior in conversion degree and selectivity could be produced easily.

The same catalyst was produced by same manner above. It also became clear that production of the above catalyst was highly reproducible.

Comparative Example 1

An additive-containing catalyst precursor obtained by the same process as employed in Example 1 was packed into the same tubular reactor as used in Example 1. An air of 30° C. was passed through the tubular reactor and, in this state, a heat medium air of 30° C. was passed round the tubular reactor in the same direction as that of the air passed through the tubular reactor. Then, the temperatures of the air passed through the tubular reactor and the heat medium air were increased each at a rate of 20° C./hr and, in this state, the heat treatment was continued for 13 hours. After 9 hours from the start of the heat treatment, the temperatures of the air passed through the tubular reactor and the heat medium air became each 210° C., the temperature of the air passed through the tubular reactor, at the inlet of the catalyst precursor layer became 210° C., and the temperature of the air at the outlet became 164° C. In the period from 9 hours from the start of the heat treatment to 11 hours from the start, the decomposed substances and vaporized substances of the additive, which accumulated at the air outlet of the catalyst precursor layer, caused violent combustion; resultantly, the air outlet showed a sharp temperature increase and reached the maximum temperature of 535° C. After 13 hours from the start of the heat treatment, the temperatures of the air passed through the tubular reactor and the heat medium air became each 290° C., the temperature of the air passed through the tubular reactor, at the inlet of the catalyst precursor layer became 288° C., and the temperature of the air at the outlet became 256° C. In the period, the maximum temperature increase per hour, of the catalyst precursor was 250° C.

Then, the temperatures of the air passed through the tubular reactor and the heat medium air were kept each at 510° C. for 6 hours, and the heat treatment of the additive-containing catalyst precursor was completed. At the completion of the heat treatment, the temperatures of the air passed through the tubular reactor, at the inlet and outlet of the catalyst precursor layer were each 510° C.

A reaction was conducted in the same manner as in Example 1, using the above-obtained catalyst. AS a result, the conversion degree of propylene was 97.3%, the selectivity of acrolein was 85.2%, and the selectivity of acrylic acid was 6.1%.

EXAMPLE 2

To 1,000 parts of pure water were added 500 parts of ammonium paramolybdenate, 12.4 parts of ammonium para-tungstate, 23.0 parts of cesium nitrate, 27.5 parts of antimony trioxide and 33.0 parts of bismuth trioxide. The resulting mixture was stirred with heating, to obtain a liquid A. Separately, to 1,000 parts of pure water were added 228.8 parts of ferric nitrate, 68.6 parts of nickel nitrate, 412.1 parts of cobalt nitrate, 23.5 parts of lead nitrate and 2.7 parts of 85% phosphoric acid in this order, to obtain a liquid B. The liquid B was added to the liquid A to obtain an aqueous slurry. The aqueous slurry was dried using a spray drier to obtain a dry powder. The dry powder was fired at 510° C. for 1 hour to obtain a fired material. 500 parts of the fired material was mixed with 180 parts of pure water and 25 parts of methyl cellulose. The resulting mixture was subjected to extrusion molding to obtain a ring-molded wet-molded material having an outer diameter of 5 mm, an inner diameter of 2 mm and an average length of 5 mm. The wet-molded material was dried by a drying method using, in combination, a microwave and hot air, to obtain an additive (methyl cellulose)-containing catalyst precursor. The temperature at which the generation of decomposed substances and/or vaporized substances from the additive-containing catalyst precursor was most violent, was 234° C. as measured by thermogravimetry.

The additive-containing catalyst precursor was packed in a stainless steel-made tubular reactor of 27.5 mm in inner diameter and 4 m in length having a mechanism for passing a heat medium round the circumference, which was provided parallel to a vertical direction.

Successively, an air of 30° C. was passed through the tubular reactor. In this state, a heat medium air preheated at 200° C. was passed as a heat medium round the tubular reactor to a direction opposite to the direction of the air passed through the tubular reactor. Immediately after the start of the passing, the temperature of the air passed through the tubular reactor, at the inlet of the catalyst precursor layer was 30° C., the temperature of the air at the outlet was 36° C., and the difference between the temperatures at the inlet and the outlet was 6° C. Passing of the preheated air was continued; 3 hours later, the temperature of the air passed through the tubular reactor, at the inlet of the catalyst precursor layer was 39° C., the temperature of the air at the outlet was 136° C., and the temperature at the outlet was 97° C. higher than the temperature at the inlet. Thereafter, the temperatures of the air passed through the tubular reactor and the heat medium air were increased each at a rate of 20° C./hr and, in this state, the heat treatment was continued for 11 hours. After 12 hours from the start of the heat treatment, the temperature of the air passed through the tubular reactor was 250° C., the temperature of the heat medium air was 420° C., the temperature of the air passed through the tubular reactor, at the inlet of the catalyst precursor layer was 285° C., the temperature of the air at the outlet was 408° C., and the temperature of the air at the outlet was 123° C. higher than the temperature of the air at the inlet. In the period, the maximum difference between the temperatures at the inlet and the outlet was 144° C. Also in the period, the maximum temperature increase per hour, of the catalyst precursor was 35° C.

Then, the temperatures of the air passed through the tubular reactor and the heat medium air were kept each at 400° C. for 6 hours, and the heat treatment of the additive-containing catalyst precursor was completed. At the completion of the heat treatment, the temperatures of the air passed through the tubular reactor, at the inlet and outlet of the catalyst precursor layer were each 400° C.

The thus-obtained catalyst had a metal composition of $Mo_{12}W_{0.2}Bi_{0.6}Fe_{2.4}Sb_{0.8}Ni_1Co_6Pb_{0.3}P_{0.1}Cs_{0.5}$. The catalyst was cooled to 340° C., after which a raw material gas consisting of 5% of isobutylene, 12% of oxygen, 10% of steam and 73% of nitrogen (% was by volume) was passed through the catalyst layer for a contact time of 3.6 seconds, to give rise to a reaction. As a result, the degree of conversion of isobutylene was 97.2%; the selectivity of methacrolein was 87.2%; and the selectivity of methacrylic acid was 3.9%.

It became clear from the above that the sintering of catalyst caused by the combustion of additive, the reduction of catalyst by additive, etc. were prevented in the step of catalyst heat treatment and that a catalyst superior in conversion degree and selectivity could be produced easily.

The same catalyst was produced by same manner above. It also became clear that production of the above catalyst was highly reproductive.

Comparative Example 2

An additive-containing catalyst precursor obtained by the same process as employed in Example 2 was packed into the same tubular reactor as used in Example 2. An air of 30° C. was passed through the tubular reactor and, in this state, a heat medium air of 30° C. was passed round the tubular reactor to the same direction as that of the air passed through the tubular reactor. Then, the temperatures of the air passed through the tubular reactor and the heat medium air were increased each at a rate of 20° C./hr and, in this state, the heat treatment was continued for 13 hours. After 9 hours from the start of the heat treatment, the temperatures of the air passed through the tubular reactor and the heat medium air became each 210° C., the temperature of the air passed through the tubular reactor, at the inlet of the catalyst precursor layer became 210° C., and the temperature of the air at the outlet became 167° C. In the period from 9 hours from the start of the heat treatment to 11 hours from the start, the decomposed substances and vaporized substances of the additive, which accumulated at the air outlet of the catalyst precursor layer, caused violent combustion; resultantly, the air outlet showed a sharp temperature increase and reached the maximum temperature of 560° C. After 13 hours from the start of the heat treatment, the temperatures of the air passed through the tubular reactor and the heat medium air became each 290° C., the temperature of the air passed through the tubular reactor, at the inlet of the catalyst precursor layer became 288° C., and the temperature of the air at the outlet became 261° C. In the period, the maximum temperature increase per hour, of the catalyst precursor was 260° C.

Then, the temperatures of the air passed through the tubular reactor and the heat medium air were kept each at 400° C. for 6 hours, and the heat treatment of the additive-containing catalyst precursor was completed. At the completion of the heat treatment, the temperatures of the air passed through the tubular reactor, at the inlet and outlet of the catalyst precursor layer were each 400° C.

A reaction was conducted in the same manner as in Example 2, using the above-obtained catalyst. AS a result, the conversion degree of isobutylene was 94.3%, the selectivity of methacrolein was 86.2%, and the selectivity of methacrylic acid was 3.6%.

Comparative Example 3

An additive-containing catalyst precursor obtained by the same process as employed in Example 2 was packed into the same tubular reactor as used in Example 2. An air of 30° C. was passed through the tubular reactor without passing a heat medium air. Then, the temperature of the air passed through the tubular reactor was increased at a rate of 20° C./hr without passing a heat medium air and, in this state, the heat treatment was continued for 16 hours. After 11 hours from the start of the heat treatment, the temperature of the air passed through the tubular reactor became 250° C., the temperature of the air passed through the tubular reactor, at the inlet of the catalyst precursor layer became 248° C., and the temperature of the air at the outlet became 162° C. In the period from 11 hours from the start of the heat treatment to 13 hours from the start, the decomposed substances and vaporized substances of the additive, which accumulated at the air outlet of the catalyst precursor layer, caused violent combustion; resultantly, the air outlet showed a sharp temperature increase and reached the maximum temperature of 585° C. After 16 hours from the start of the heat treatment, the temperature of the air passed through the tubular reactor became 350° C., the temperature of the air passed through the tubular reactor, at the inlet of the catalyst precursor layer became 348° C., and the temperature of the air at the outlet became 285° C. Then, a heat medium air was passed to a direction opposite to the direction of the air passed through the tubular reactor; the temperatures of the air passed through the tubular reactor and the heat medium air were kept each at 400° C. for 6 hours, and the heat treatment of the additive-containing catalyst precursor was completed. At the completion of the heat treatment, the temperatures of the air passed through the tubular reactor, at the inlet and outlet of the catalyst precursor layer were each 400° C. In the period, the maximum temperature increase per hour, of the catalyst precursor was 255° C.

A reaction was conducted in the same manner as in Example 2, using the above-obtained catalyst. As a result, the conversion degree of isobutylene was 90.8%, the selectivity of methacrolein was 86.8%, and the selectivity of methacrylic acid was 4.0%.

EXAMPLE 3

A reaction was conducted in the same manner as in Example 2 except that the isobutylene in the raw material gas was changed to TBA. As a result, the conversion degree of TBA was 100%, the selectivity of methacrolein was 84.1%, and the selectivity of methacrylic acid was 3.7%.

Comparative Example 4

A reaction was conducted in the same manner as in comparative Example 2 except that the isobutylene in the raw material gas was changed to TBA. AS a result, the conversion degree of TBA was 100%, the selectivity of methacrolein was 80.9%, and the selectivity of methacrylic acid was 3.3%.

INDUSTRIAL APPLICABILITY

As is clear from the above description, when, in producing a catalyst used for synthesis of an unsaturated aldehyde and an unsaturated carboxylic acid by a gas-phase catalytic oxidation, there is used a step of packing an additive-containing catalyst precursor of the catalyst into a tubular reactor, passing a gas through the tubular reactor, and elevating, in this state, the temperature of the additive-containing catalyst precursor so that a temperature of the gas at an outlet of the catalyst precursor layer becomes higher than a temperature of the gas at an inlet of the catalyst precursor layer, there can be produced easily at a high reproducibility a high-performance catalyst which is small in the reduction in catalytic performance caused by, for example, the thermal decomposition of the additive contained in the catalyst precursor.

What is claimed is:

1. A process for producing a catalyst for producing an unsaturated aldehyde and an unsaturated carboxylic acid by a gas-phase catalytic oxidation, which comprises the steps of:

packing a layer of an additive-containing catalyst precursor into a tubular reactor; and elevating the temperature of the additive-containing catalyst precursor, while passing a gas through the tubular reactor, so that the gas at an outlet of the catalyst precursor layer has a temperature which is higher than the temperature of the gas at an inlet of the catalyst precursor layer.

2. A process for producing the catalyst according to claim 1, wherein, while elevating the temperature of the additive-containing catalyst precursor, at least a part of the additive-containing catalyst precursor is heated to at least a temperature at which the mass of the additive-containing catalyst precursor decreases most sharply due to a change of the additive.

3. A process for producing the catalyst according to claim 1, wherein the temperature of the additive-containing catalyst precursor is elevated by flowing a heated medium around the tubular reactor containing the catalyst precursor layer, in a direction opposite to the direction in which the gas inside the tubular reactor flows.

4. A process for producing the catalyst according to claim 3, wherein, the heated medium flowing around the tubular reactor has an initial temperature of 20° C. to 400° C.

5. A process for producing the catalyst according to claim 1, wherein, while elevating the temperature of the additive-containing catalyst precursor, the temperature of the gas passing through the tubular reactor, at the inlet of the catalyst precursor layer, is increased to at least a temperature at which the mass of the additive-containing catalyst precursor decreases most sharply due to a change of the additive.

6. A process for producing the catalyst according to claim 1, wherein, while elevating the temperature of the additive-containing catalyst precursor, the temperature of the gas passing through the tubular reactor at the inlet of the catalyst precursor layer is increased to a temperature in the range of 100° C. to 600°C.

7. A process for producing the catalyst according to claim 1, wherein, while elevating the temperature of the additive-containing catalyst precursor, the gas passing through the tubular reactor has a maximum temperature difference, at the inlet and outlet of the catalyst precursor layer, of 10° C. to 400° C.

8. A process for producing the catalyst according to claim 1, wherein the catalyst catalytically oxidizes, in the gas phase with a molecular oxygen, at least one compound selected from the group consisting of propylene, isobutylene, tert-butyl alcohol and methyl tert-butyl ether.

9. A process for producing the catalyst according to claim 1, wherein the catalyst comprises at least molybdenum, bismuth and iron.

10. A process for producing the catalyst according to claim 1, wherein the additive is at least one compound selected from the group consisting of natural polysaccharides, cellulose, polystyrene, polymethyl (meth) acrylate, animonium nitrate and derivatives thereof.

11. A process for producing the catalyst according to claim 10, wherein the additive comprises at least a cellulose derivative.

12. A tubular reactor filled with a catalyst for producing an unsaturated aldehyde and an unsaturated carboxylic acid by a gas-phase catalytic oxidation;

wherein the catalyst is made by a process comprising the steps of:

packing a layer of an additive-containing catalyst precursor of the catalyst into the tubular reactor; and elevating the temperature of the additive-containing catalyst precursor, while passing a gas through the tubular reactor, so that the gas at an outlet of the catalyst precursor layer has a temperature which is higher than the temnerature of the gas at an inlet of the catalyst precursor layer.

13. A process for producing an unsaturated aldehyde and an unsaturated carboxylic acid, comprising catalytically oxidizing propylene, isobutylene, tert-butyl alcohol or methyl tert-butyl ether in the gas-phase with a molecular oxygen in the tubular reactor according to claim 12.

* * * * *